United States Patent [19]

Voroba et al.

[11] Patent Number: 4,759,070

[45] Date of Patent: Jul. 19, 1988

[54] PATIENT CONTROLLED MASTER HEARING AID

[75] Inventors: Barry Voroba, Minnetonka; James P. Wilkinson, Richfield, both of Minn.

[73] Assignee: Voroba Technologies Associates, Minnetonka, Minn.

[21] Appl. No.: 867,487

[22] Filed: May 27, 1986

[51] Int. Cl.⁴ .......................... A61N 1/36; H04R 25/00
[52] U.S. Cl. .................................... 381/60; 381/68.6; 128/746
[58] Field of Search ................. 381/60, 68.2, 68, 68.6; 128/746

[56] References Cited

U.S. PATENT DOCUMENTS

| | | | |
|---|---|---|---|
| 3,784,750 | 1/1974 | Stearns et al. | 381/68.2 |
| 3,818,149 | 6/1974 | Stearns et al. | 381/68.2 |
| 3,989,904 | 11/1976 | Rohrer et al. | 381/68.2 |
| 4,099,035 | 7/1978 | Yanick | 381/68.2 |
| 4,471,171 | 9/1984 | Köpke | 381/60 |
| 4,575,586 | 3/1986 | Topholm | 381/68.2 |
| 4,577,641 | 3/1986 | Hochmair | 381/68.2 |
| 4,637,402 | 1/1987 | Adelman | 381/68.2 |

OTHER PUBLICATIONS

*Hearing Aid Journal*, article entitled "New Master Hearing Aid with Flexibility for Research", Martin, Apr., 1981, pp. 7, 39–41.
*Amplification for the Hearing-Impaired*, Ed. Pollack, "Chapter 9: The Search for a Master Hearing Aid", Berger 1980; New York, Grune & Straton; pp. 305–322.
*Application of Signal Processing Concepts to Hearing Aids*, "Chapter 5: The Master Hearing Aid", Franks, 1978; pp. 85–124.
*Perspectives on the State of Hearing Aid Fitting Practices*, Voroba, four page pamphlet reprinted from article published in *Audecibel*, vol. 31(2), 1982, pp. 12–16.
*A Tool for the Optimization of Hearing Aid Fittings*, Voroba, four page pamphlet reprinted from article published in *Hearing Instruments*, Jan. 1984.

*Sound Pressure Instruments*, published in "Hearing Instruments", Feb. 1977.

*Primary Examiner*—Thomas W. Brown
*Assistant Examiner*—L. C. Schroeder
*Attorney, Agent, or Firm*—Dorsey & Whitney

[57] ABSTRACT

A programmable patient controlled master hearing aid is disclosed which consists of a hearing aid test module, an operator's console and a patient's console, both of which are microprocessor based, and all of which are interconnected to provide a testing apparatus which is used by the patient to select electronic components to be imployed in a hearing aid. The testing device has selectable electronic components that match the components which will be used in the hearing aid which the patient selects as best assisting or addressing the patient's hearing loss. The patient is located in the center of a sound field created by multiple speakers which accurately reproduce both pre-recorded environmental background sounds and pre-recorded or live "target-stimuli" such as speech. Thus surrounded by a simulation of real-world listening situations, the patient initially selects a hearing aid shell assembly which comfortably fits in the patient's ear. A test module which is connected to the patient's console is then employed which snaps into the hearing aid shell assembly and provides decision tree choices of electronic components and concomitant sound qualities which the patient chooses by listening to various combinations of components and sound conditions. The patient chooses those components which give the most acceptable amplification and performance characteristics, which best address the patient's hearing loss. Similarly, tinnitus conditions can be addressed as well.

After the patient has completed the test procedure and selected those components which best address the patient's hearing condition, electronic components with the same specifications as those used during testing are snapped into the earshell assembly used during the test so that the patient can leave with the hearing aid that he or she has selected.

18 Claims, 11 Drawing Sheets

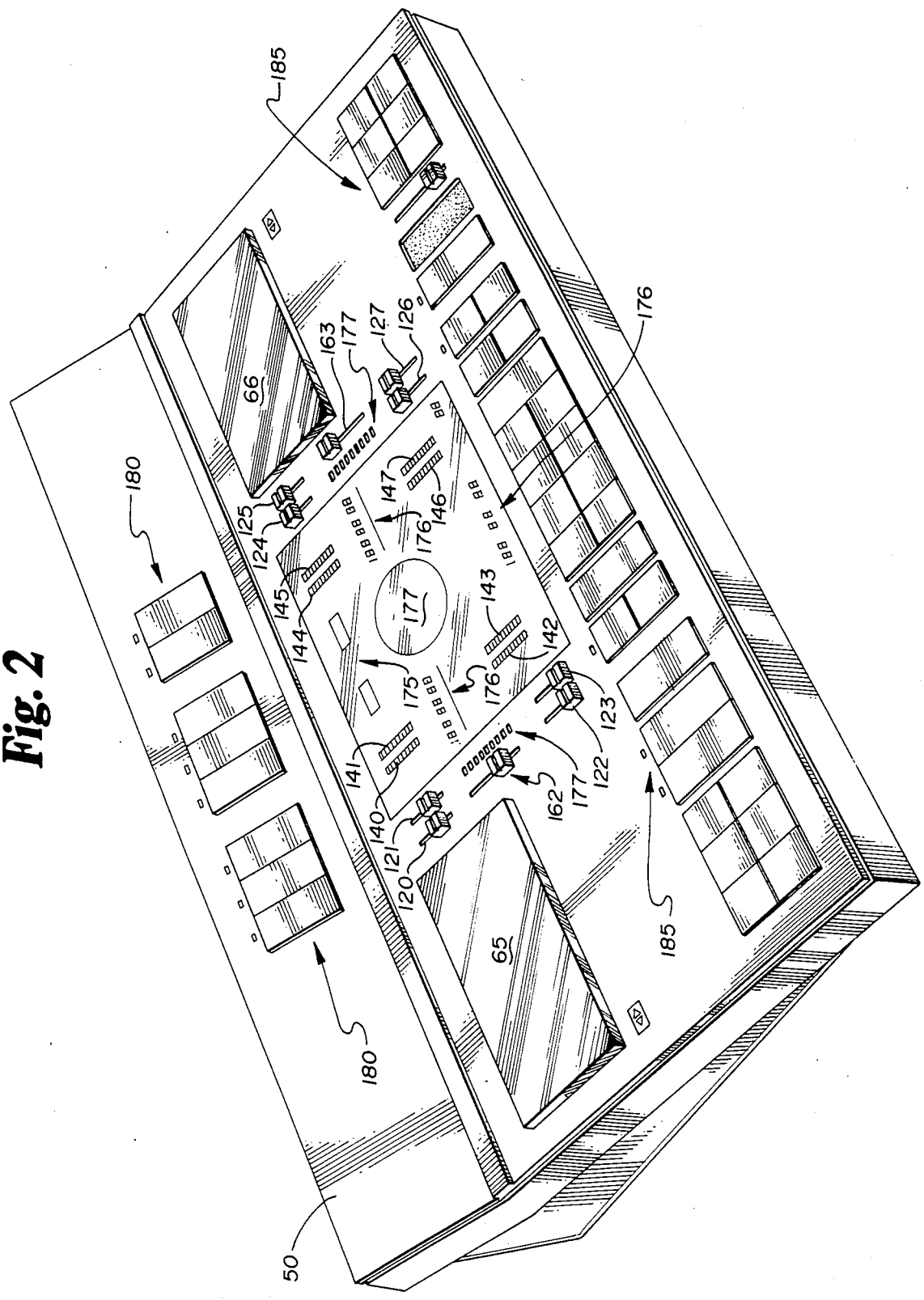

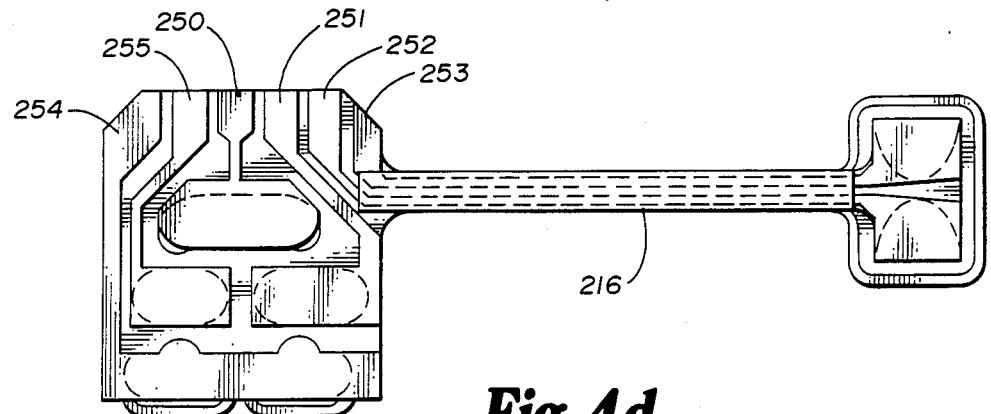
Fig. 4c
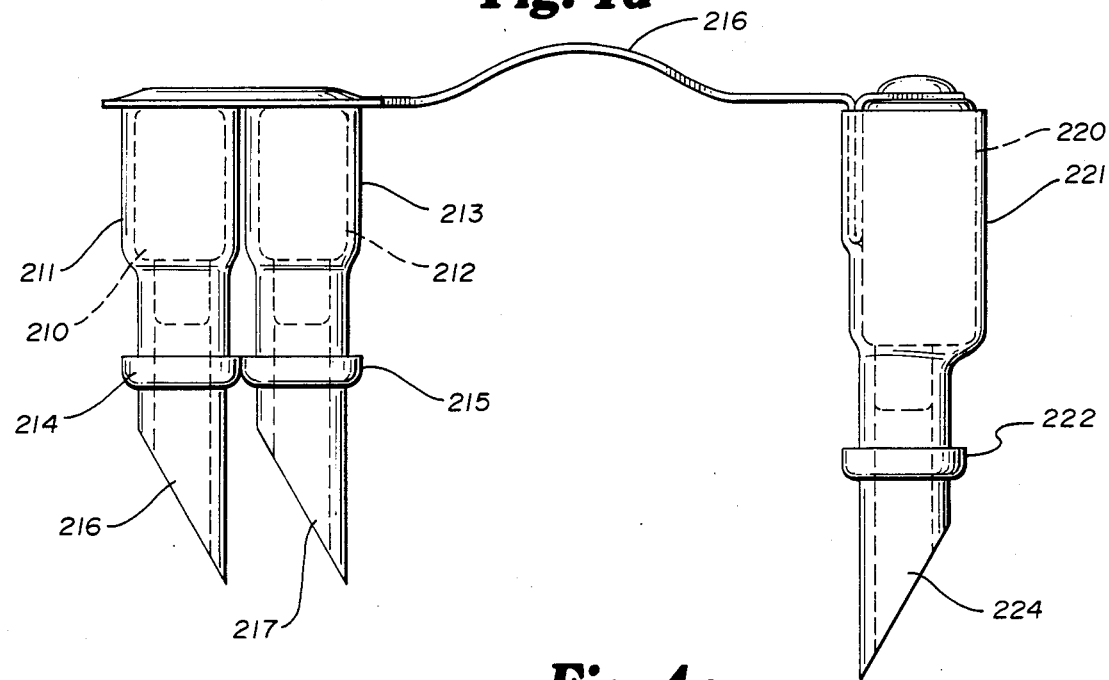
Fig. 4d
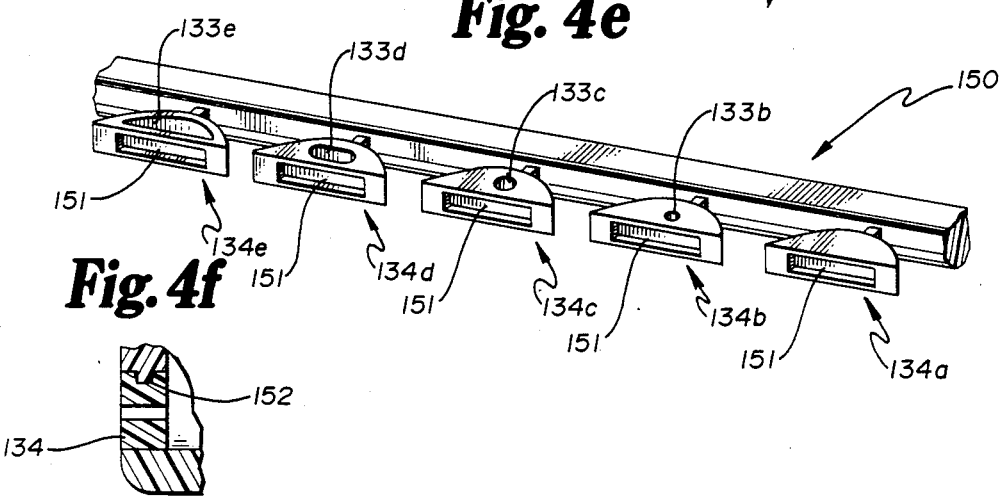
Fig. 4e
Fig. 4f

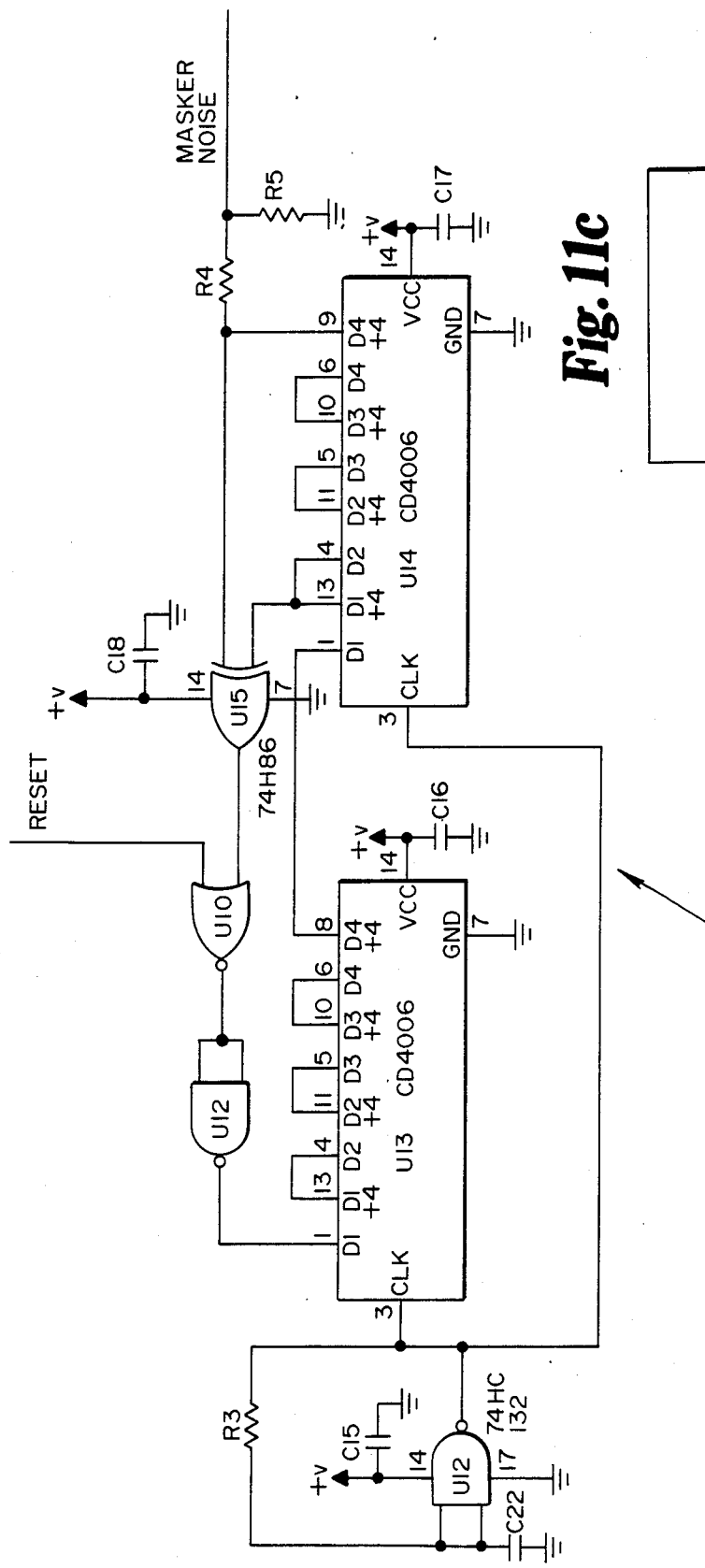
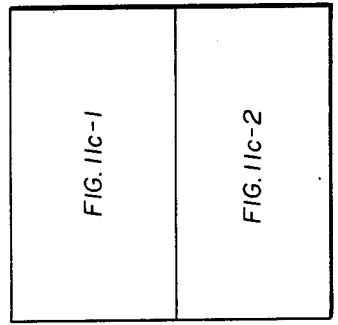

PATIENT CONTROLLED MASTER HEARING AID

RELATED APPLICATION

This application is related to U.S. patent application Ser. No. 868,117, entitled Mass Production Auditory Canal Hearing Aid, filed May 27, 1986, which more fully describes the hearing aid assembly which is provided by use of the invention described in this application.

DESCRIPTION OF THE PRIOR ART

The invention relates to testing devices used to select a hearing aid prosthesis. More particulary, the invention comprises a device which is connected to a test module placed in a patient's ear to selectively combine various electronic components used in the design of a hearing aid. Using the device, the patient may select those electronic components which combine to yield amplification which best assists the patient's hearing loss or hearing impediment so that a patient selected hearing aid may be provided which the patient has identified as being most preferred for the patient's unique hearing characteristics and defects.

Hearing aids have been prescribed and provided in the past based on the results of audiometric testing procedures which include hearing threshold tests wherein various sinusoidal tones of differing frequency are transmitted through a set of headphones and patient indicates at which lowest level the sound is first detectable. The professional then charts or plots the results of the acuity or threshold testing on an "audiogram" and evaluates the hearing loss within the context of conventional hearing standards and norms. One of many currently popular (and often disparate) fitting philosophies is then employed to "prescribe" the performance characteristics of a hearing aid which the professional believes will effectively amplify those sound frequencies which the test results indicate deviate from the norm. Alternatively, and more commonly, the audiogram and an impression of the patient's ear are sent to a hearing aid manufacturer and a design technician assumes the responsibility for prescribing a circuit for the device.

There are many problems inherent to the use of current audiometric testing procedures for the prescription and provision of hearing prosthesis. Many limitations are related to the complex acoustics, physiology and psycho-acoustics of human hearing and which are not adequately addressed by simple acuity or threshold testing. For example, the important acoustic influences of the external ear and its natural role in human hearing are not considered by conventional audiometric tests which occlude the ears with headphones. The Pinna or Auricle (i.e. outer flap) and concha or "bowl" of the ear are anatomical features which effectively gather sound emanating from the environment. The multiple reflections of sounds from the crenulations of the Pinna into the meatus or canal of the ear as well as the diffraction or bending of selected sound frequencies around the obstacle of the head all serve to assist a listener in identifying the location of sound sources in three-dimensional space and in selectively attending to important signals in noisy environments. These factors become especially important for binaural hearing (i.e., hearing with both ears).

In addition, the electroacoustic characteristics of headsets or earphones conventionally used in audiometric testing or previous master hearing aid simulators are usually substantially different from those of the miniaturized receivers used in hearing aids, thereby rendering predictions and prescriptions of appropriate frequency response between systems employing different types of transducers quite difficult and unreliable. Attempts to predict and prescribe meaningful and effective hearing aid fittings with headphone equipped instrumentation are further confounded by the fact that the sound output of a hearing aid is altered by the resonant characteristics of the individual's own ear canal, along with a variety of other acoustic effects which arise from the interplay between the hearing aid and such factors as canal insertion depth, ear geometry, frequencies in the amplified signal, standing waves and the impedance of the eardrum. These same phenomena also render recent efforts to use miniature microphones for in-situ (i.e., in the canal) measurement of hearing aid characteristics in the prescription and fitting process prone to error.

Perhaps the most serious shortcoming to contemporary hearing aid prescription philosophies, procedures and instrumentation lies with the understandable but somewhat paternalistic viewpoint that the professional knows what the patient will prefer despite the aforementioned limitations in the measurement and understanding of the exact relationship between audiometric test results and appropriate selection of amplification for the patient. Hearing is, after all, a sensation that intimately involves highly complex, subjective perceptions and reactions from a listener; not just his or her pure tone threshold levels or the voltage readings associated with them.

In the past, there has been a high level of dissatisfaction or rejection of the hearing aid after it has been fabricated by the factory and returned to the dispenser for delivery to the patient. Consequently, many hearing aids which are judged unsatisfactory by the patient are returned to the dispenser and a warranty repair takes place wherein the hearing aid is refabricated at the factory. This often hit and miss repeated return practice in the hearing aid industry has caused warranty repair of hearing aids to be the single largest expense in the hearing aid industry. Since any retesting and refabrication suffers from the same problems as the original prescription, the final hearing aid delivered may not be substantially better than the original hearing aid prescribed.

What has been lacking in the prior attempts to create a master hearing aid testing apparatus is a device which permits the patient to be an intimate and important part of the selection process. It is necessary that the patient communicate his or her amplification preferences fully during the testing process. The patient must then be able to receive a hearing aid which matches as closely as possible the sound quality and other performance characteristics which were preferred during the evaluation.

SUMMARY OF THE INVENTION

The patient controlled master aid of the instant invention is a fully integrated apparatus which allows the patient to be the primary decision maker in the selection process of the prescription for the hearing aid that will be provided. The patient initially selects an earshell assembly which comfortably and accurately conforms to the patient's own ear canal, both to the diameter of the ear canal and to the specific geometry of the patient's ear canal. This earshell assembly is the earshell assembly that is used during the testing process and is also the earshell assembly that will be used for the patient's hearing aid. Therefore, resonant and other acoustic characteristics of the patient's ear canal are addressed and become part of the testing process. A test module is then inserted into the earshell assembly which employs one or more receivers and microphones, used to provide a variety of hearing aid response characteristics. One of these microphones will be selected and will have the same manufacturer's specifications as the microphone that will actually be used in the patient's hearing aid. These test module transducers are connected by a cable to the patient's console.

Two microprocessor based test consoles are provided, one for the patient and one for the tester. One function of the operator's console is to establish sound field test conditions which simulate as closely as possible the patient's listening experience in the patient's own environment. Tape decks are provided for the presentation of a "target stimulus" (e.g., continuous discourse) and environmental "ambience" (e.g., background noise or competing speech signals). Outputs from the tape decks are electronically mixed and preferably provided in a multiphonic sound field around the patient, that is, with sound emanating toward the patient from many directions.

During testing the electronic characteristics of the hearing aid itself are fully explored by the patient. The patient, by paired comparative selections, chooses the electronic components that will give the preferred saturation sound pressure level (S.S.P.L.), the preferred gain of the hearing aid and the preferred frequency response slope of the sound. S.S.P.L. is defined as the peak acoustic output over the frequency range with 90 dB SPL input. Gain is defined to be the peak acoustic gain with 60 dB SPL input over the entire frequency range. Slope is defined as the difference between the acoustic gain at 500 Hz and the peak gain.

The electronic components which establish the maximum or saturation sound pressure level of the aid, the amplification gain of the aid and the slope of the frequency response of the aid are presented to the patient in a paired comparison, decision tree format. The decision tree can be automatically presented under microcomputer control or can be manually presented by the tester from the operator's console. Two parameters are initially set or fixed and the patient steps through choices of the third parameter, indicating the preferred sound quality which best assists the hearing loss. That parameter and one of the remaining parameters are then set and fixed and the patient comparatively evaluates the second variable parameter. The patient's choices are indicated by touching one of two switch panels on the patient's console indicating, for example, whether minimum or maximum low frequency emphasis amplification is preferred within a sound field of "target-stimuli" and environmental "ambience" which emanate from the speakers that surround the patient. Thereafter, the first two selected parameters are fixed and the patient selects the third parameter based on the previously selected conditions. Because of the ease with which the decision tree can be pursued, the test may be repeated a number of times with a different first parameter being selected for each of the sequence of tests. If a different sequence produces a slightly different result, the two selections can be compared in tournament fashion so that the best sound response can be selected by the patient.

The circuit elements that establish the sound pressure level, the gain and the slope during the testing process, including the microphone, amplifier and receiver, are the same circuit elements or have the same specifications as those that will be provided in the final hearing aid selected by the patient.

After the test has been completed and the test module is removed from the earshell assembly, an amplification module is provided by the dispenser having the same electronic components that the patient selected during testing. That amplification module is snapped into the earshell assembly which the patient selected prior to testing and the patient may leave the premises with the same hearing aid that the patient has chosen during the testing process.

It is an objective of the invention to fully involve the patient in the testing process for selection of the hearing aid.

It is an objective of the invention to provide a patient with a hearing aid with electronic components which match the electronic and acoustic components selected during the testing process.

It is an objective of the invention to provide a hearing aid during a single visit to the dispenser's office.

It is an objective of the invention to quickly and promptly identify the preferred characteristics of a hearing aid for a specific patient's hearing loss and to provide that hearing aid to the patient during the same office visit that the patient is tested.

These and other objectives and advantages of the inventoin will become apparent from a review of the following description of a preferred embodiment and the accompanying drawing and claims.

DESCRIPTION OF THE DRAWINGS

FIG. 10, consisting of FIGS. 10a, 10b and 10c, shows a representative decision tree which may be controlled by the operator of the master console or automatically by software. The patient is presented with a tournament of paired comparison choices from which the preferred S.S.P.L., gain and slope must be selected from the available electronic circuit component combinations.

DESCRIPTION OF THE PREFERRED EMBODIMENT

In 1984, one of the inventors of the described invention proposed a rationale for a new system for optimizing hearing aid fittings. In *A Tool For the Optimization of Hearing Aids Fittings* Dr. Barry Voroba submitted that there are two essential elements to achieve such optimization. The first essential element is that the burden of hearing aid selection should be shouldered more fully by the hearing impaired listener through the use of valid and effective psychoacoustic tasks. The second essential element proposed was that there be precise and accurate correspondence between the sound which the listener preferred during amplification selection and the sound delivered by the hearing aid he or she received. The instant invention is based on that proposal and achieves those two essential elements.

Prior to employing the apparatus of this invention to provide a hearing aid it is preferred that the patient undergo a thorough medical and audiometric evaluation to be sure that amplification is the appropriate course of action and the patient is a candidate for a hearing aid. It is preferred that the cause and source of any hearing impediment whether it be tinnitus or a hearing loss be thoroughly medically evaluated as to both its source and possible medical solution before the impediment is adjudged permanent and appropriate for a hearing aid or masking sound source of the type proposed. Hearing problems can also be the result of other and more severe medical problems which should and must be addressed.

If it is determined that the hearing impediment is not symptomatic of another treatable condition and is suitable for assistance by a hearing aid, then the instant invention is designed for use by a dispenser in conjunction with the patient to select a hearing aid to specifically help the patient in overcoming the handicapping aspects of the loss or condition.

Figure 1:
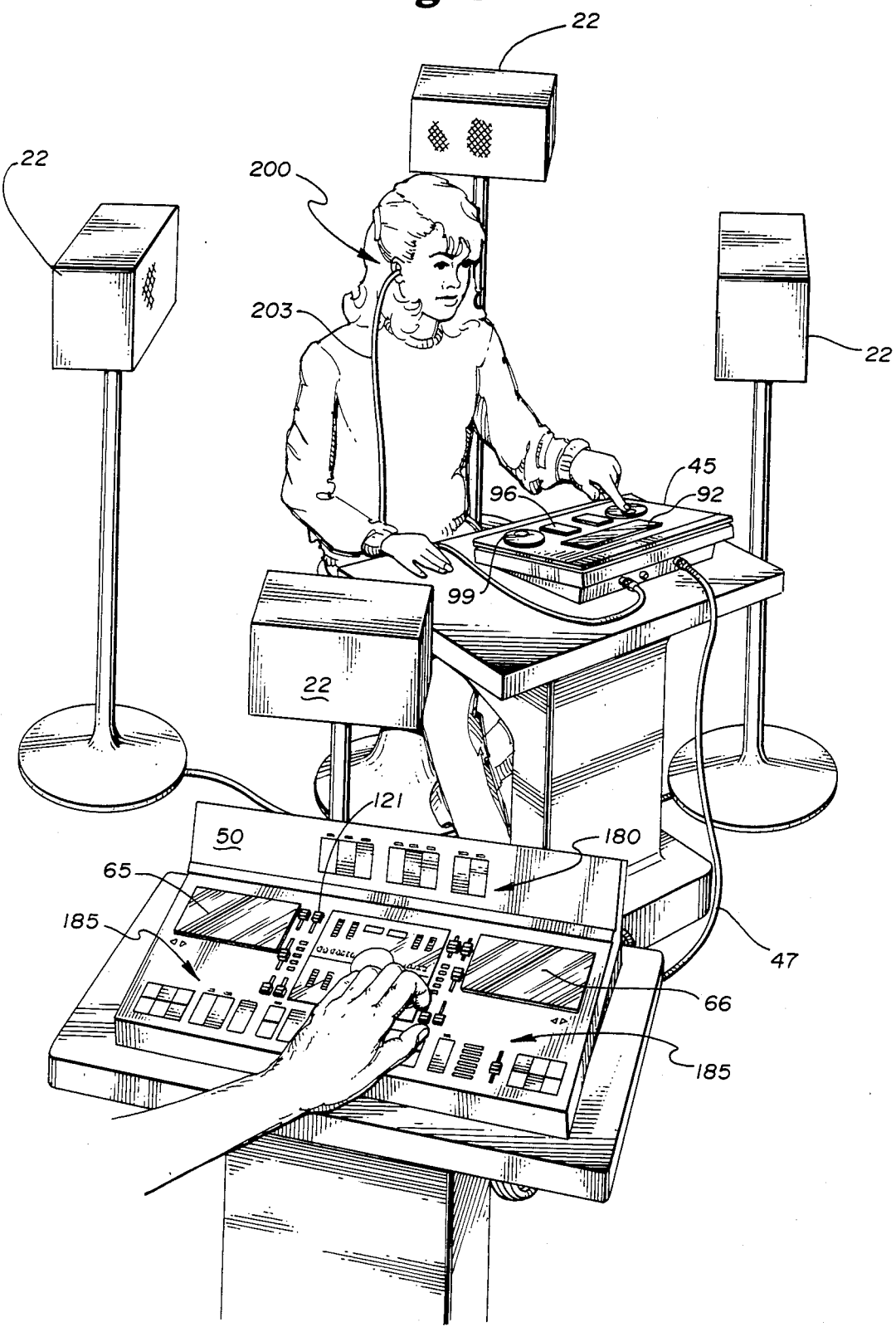
FIG. 1 is a graphic representation of the testing environment in which the patient is positioned within a quadraphonic sound field and is provided with a test module in an earshell assembly connected to a patient console which is interconnected to an operator's console for purposes of the test.

FIG. 1 shows a preferred test arrangement to enable the patient to comparatively select the proper electronic components 60 to be utilized in the patient's hearing aid so that the aid has those amplification characteristics which the patient prefers.

The patient is preferably situated in a sound field listening environment such as that shown in FIG. 1 with a plurality of speakers 22 arrayed around the patient's head so that the natural hearing environment in which the aid is to used can be recreated. The speaker array is situated so that the physical design and natural acoustic characteristics of the head and human hearing mechanism are fully utilized during the evaluation. These factors include the sound diffractive attributes of the head, the gathering and funneling of sound into the ear canal by the Pinna, and the multiple sound reflections produced by the crenulations of the Pinna. In such a sound field listening situation, the signals arriving at the ears encompass these phenomena and provide the brain with differential time and intensity sound cues which assist a listener in discerning the nature, direction, and distance of sound sources.

Prior to beginning the test the patient personally selects an earshell assembly for the aid that the patient will receive by selecting a specially designed, human engineered and sculpted earshell assembly 12 of the type which is fully disclosed in co-pending patent application Ser. No. 868,117, filed May 27, 1986 entitled "A Mass Production Auditory Canal Hearing Aid". The disclosure of that application is incorporated herein by reference and those skilled in the art are referred to that application for the design of the hearing aid suitable for use with the instant invention. A test module or assembly 200 which is shown in FIG. 4 having two microphones 210, 212 and a receiver 220 and connected by an umbilical cord 203 to the patient console 45 is inserted into the hearing aid earshell 12. Since the same earshell assembly 12 is employed for testing purposes and as the earshell assembly 12 for the final and finished hearing aid, the acoustical properties of the earshell assembly 12, including feedback properties and venting, will not vary between the test and the actual use of the aid.

Figure 4A:
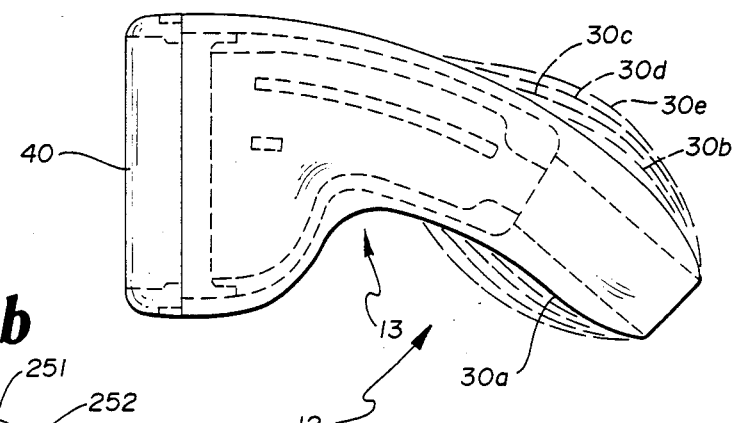
FIG. 4, consisting of FIGS. 4a-4f, show the various components used in the earshell assembly and test module which is fit in the patient's ear for purposes of the testing.
Figure 4B:
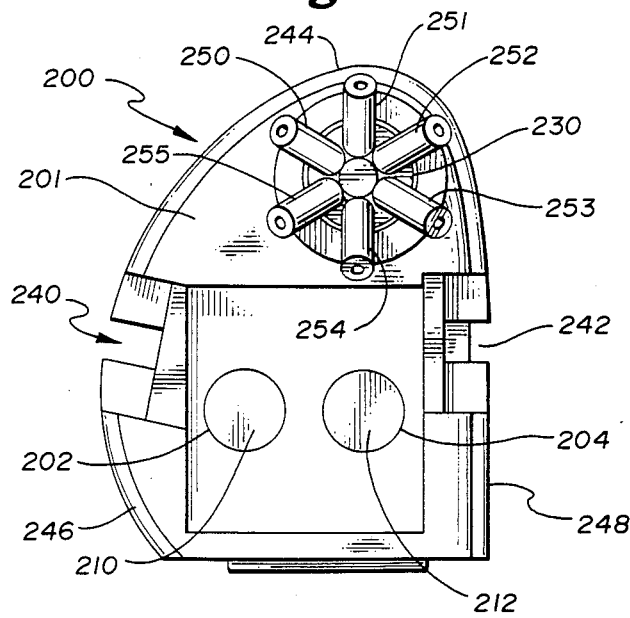

Shown in FIG. 4a is a representation of an earshell assembly 12 with a distinctive forward and inward hook and an upward twist. One of five standardized earshell coverings 30a-30e is employed, the covering being soft and malleable, to seal to the skin of the ear canal and to conform to the geometry of the canal. A test module 200 having a combined hearing aid speaker 220 and two cushioned selectable microphones 210, 212 interconnected by a flexible substrate 216 shown in FIGS. 4c and 4d are mounted in a removable cover 201 module shown in FIG. 4b. The microphones 210, 212 extend through the apertures 202, 204 in the cover 201 and the cover 201 is detachably retained by the flange 40 of earshell assembly 12 and collar segments 244, 246. The six leads 250-255 to and from the receiver 220 and microphones 210, 212 are connected to the umbilical cord 203 from the top of the test cover module 200.

Figure 3:
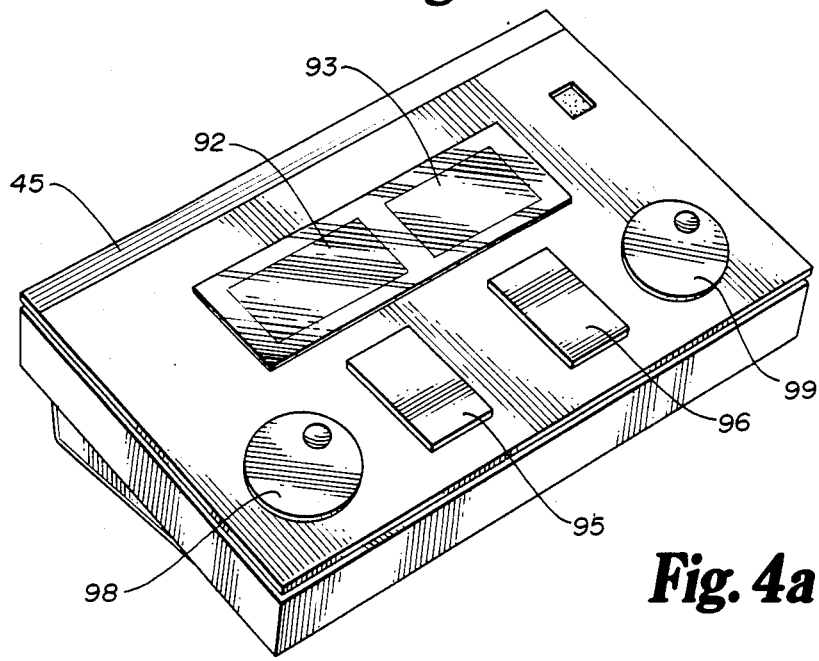
FIG. 3 is a representation of the patient's console which the patient utilizes to comparatively choose the sound characteristics of a hearing aid which best addresses the patient's hearing impediment.
Figure 11A:
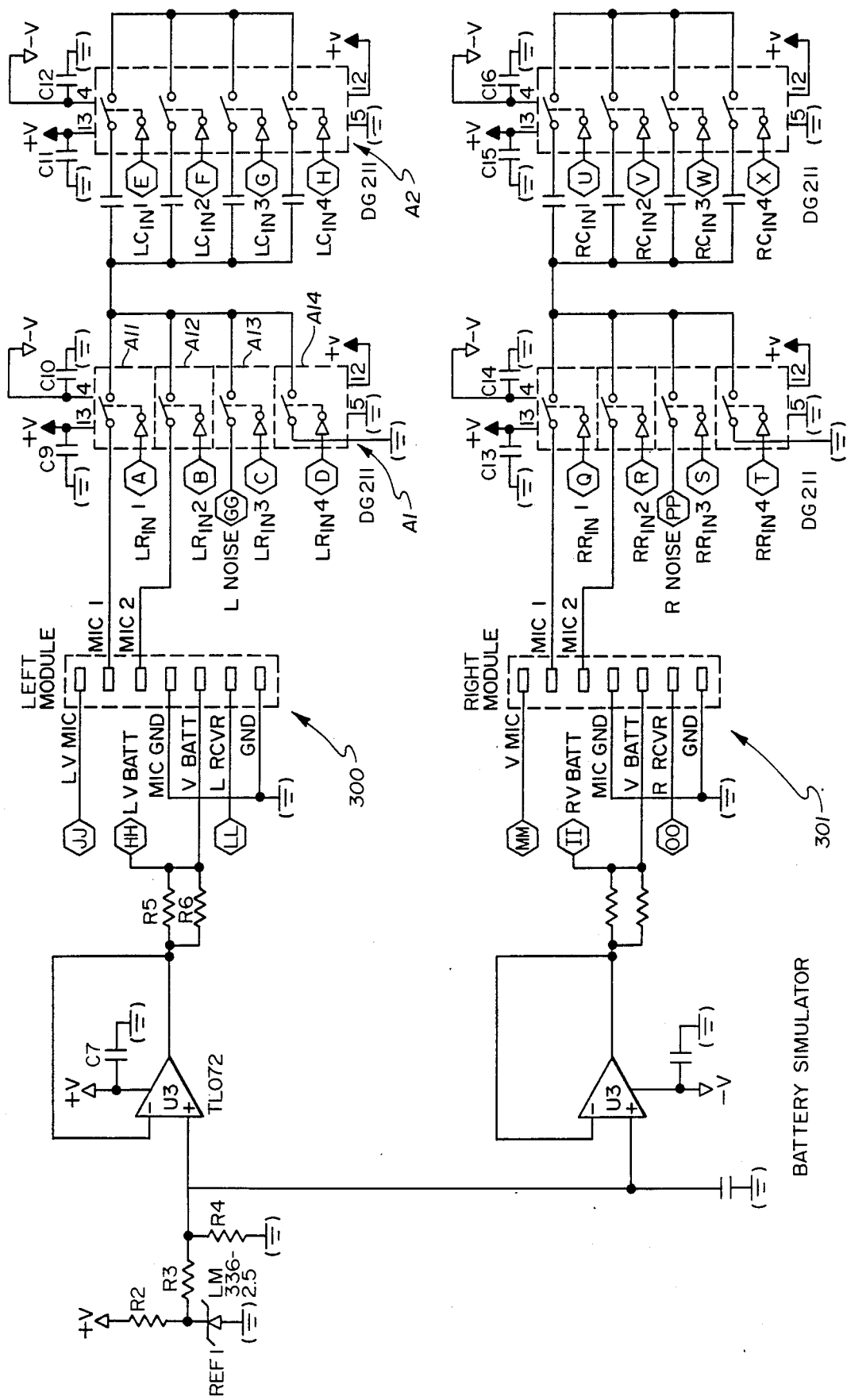
FIG. 11, consisting of FIGS. 11a-11c are schematic drawings of circuits which are used to select electronic components which will be matched by the electronic components of the final aid.
Figures 1, 11C:
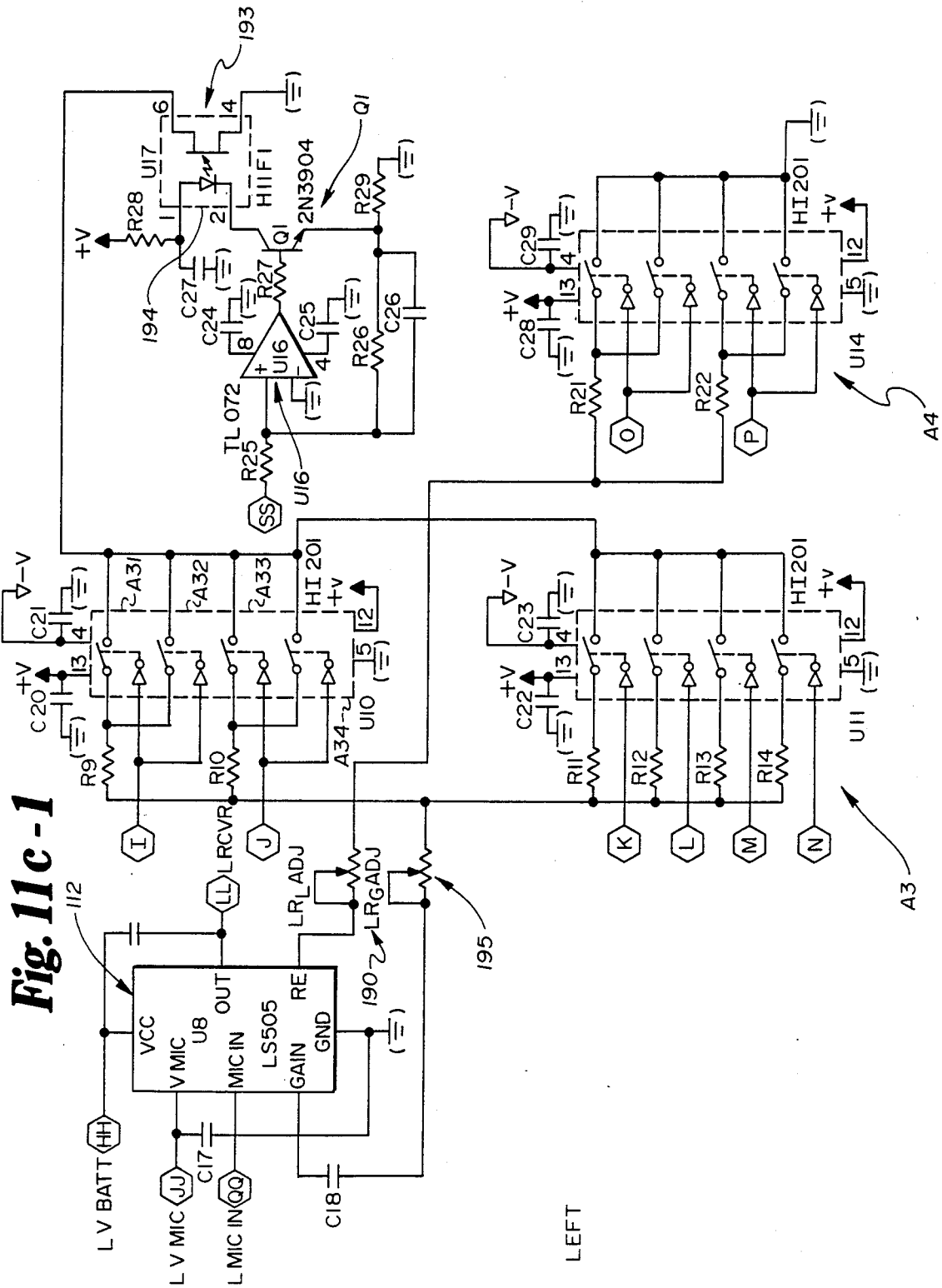
Figures 2, 11C:
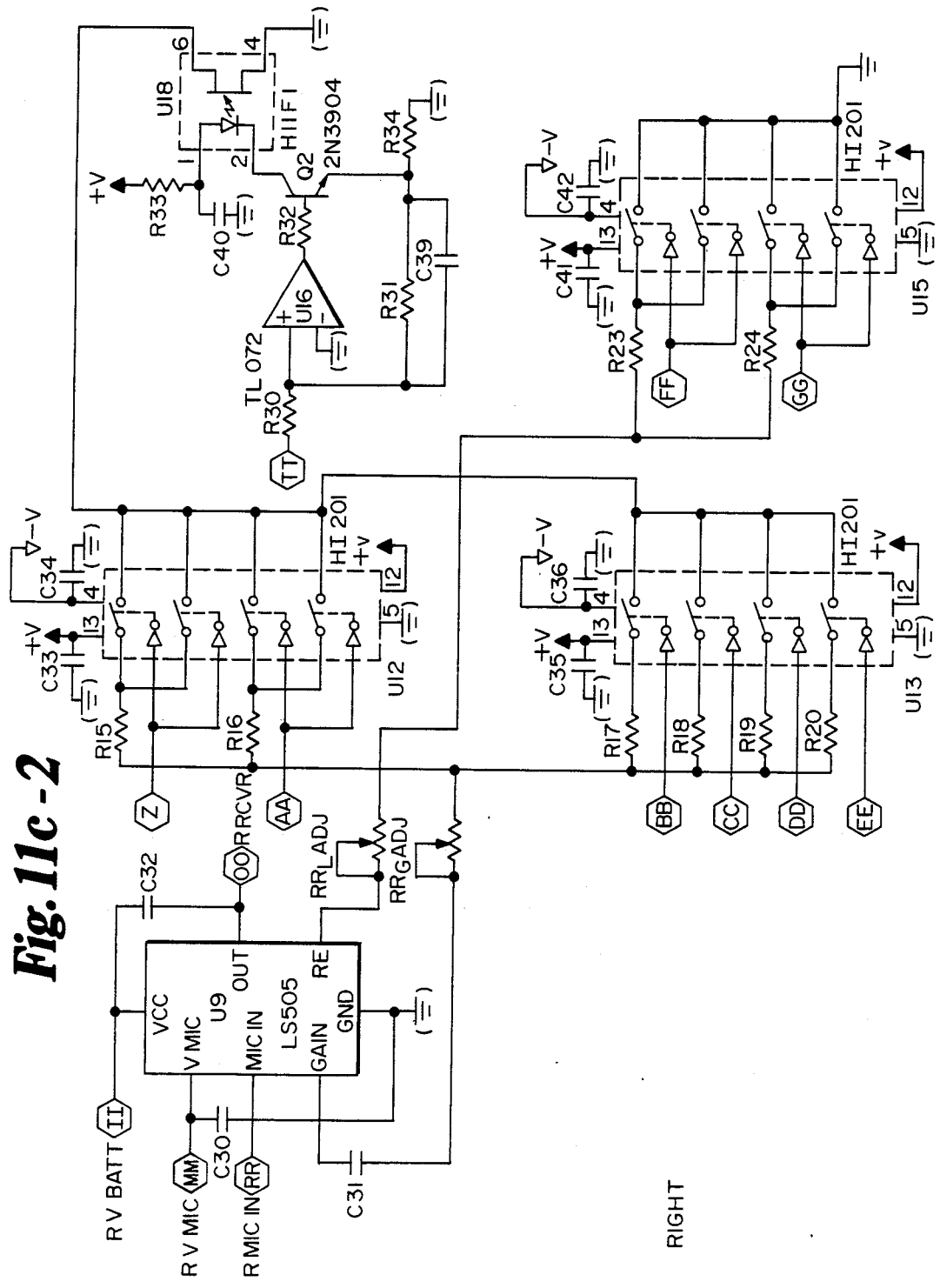
FIG. 2 is a representation of the operator's console showing the controls which the dispenser manipulates to establish the test conditions.

As shown in FIG. 1, the umbilical cord 203 from the test module 200 is connected to the patient console 45 shown in FIGS. 1 and 2 and the patient console 45 is interconnected by a cable 47 to the test console 50 as shown in FIGS. 1 and 3. As will be explained in more detail in connection with the schematic diagrams of FIG. 12, both microphones 210, 212 can be electronically disconnected to make them non-operable and a random noise generator connected to the amplifier 220 for purposes of tinnitus masking.

After the patient selects the appropriate earshell assembly 12 the test module 200 is snapped into the earshell 12 and the assembly 12 is placed in the patient's ear. Components determining electrical characteristics are set to initial values and sound stimuli and ambience presented through the speakers 22. The patient can then be asked to choose one of a plurality of vent inserts 134a-134e shown in FIGS. 4c and 4d. Venting of air from the environment to the eardrum avoids a plugged feeling of the ear and also serves a variety of acoustic functions. The patient selectable size of the vent aperture 133b-133e can, for example, be used to enhance or reduce low frequency sound energy such as may be contained in environmental noise.

Figure 5:
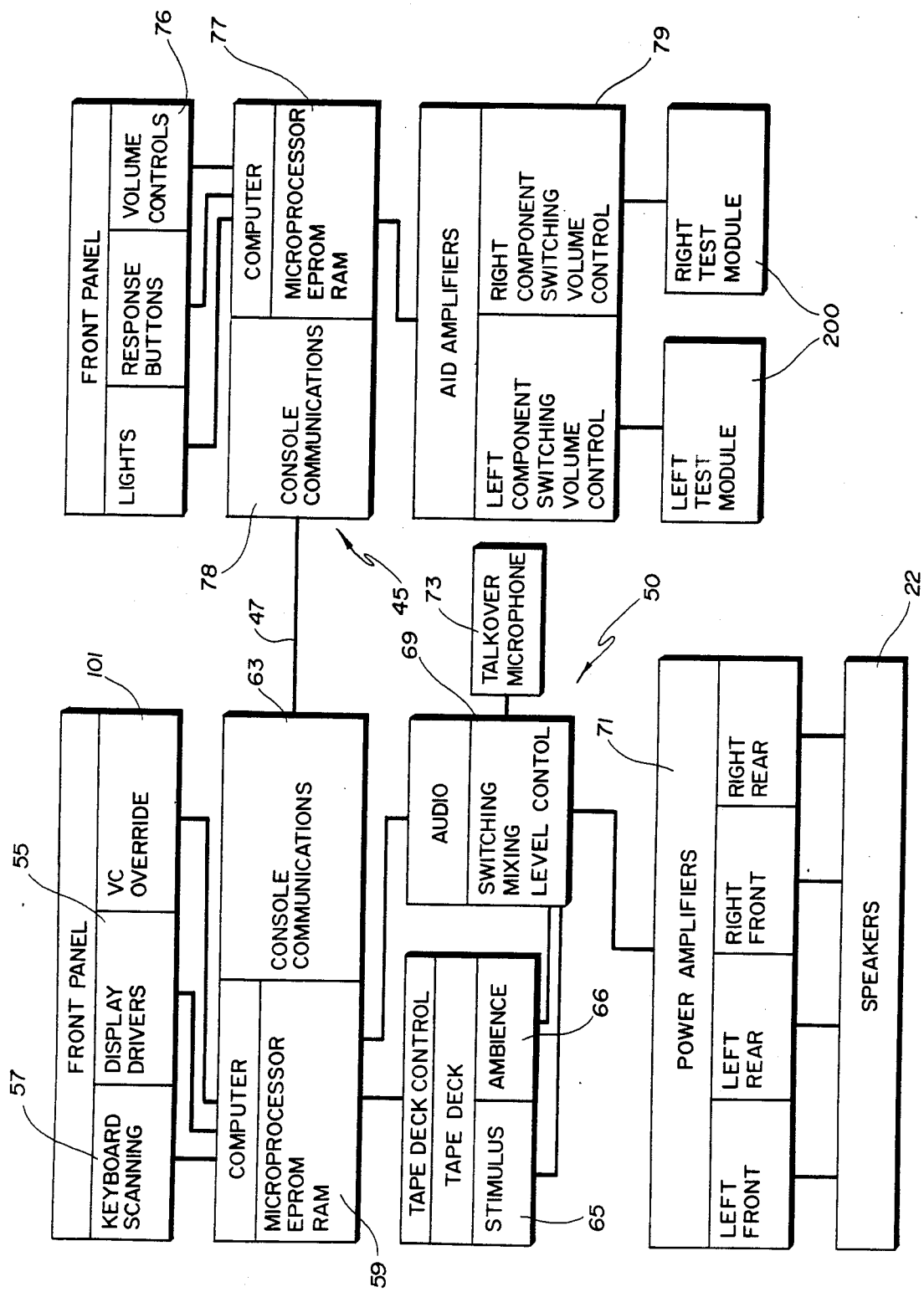
FIG. 5 is a block diagram of the modules or boards used in the operator's or master console and the patient or subject console.

Referring now to FIG. 5, the basic circuit modules of the master console 50 and the subject console 45 are shown and can be understood.

The master console includes electronic circuit modules for the front panel displays 55 and controls 57, a microcomputer 59 for control and communications 63 between the master console 50 and the subject console 45, and a stimulus and ambience tape deck 65, 66 to produce the environmental sound field. Both tape decks 65, 66 are connected to an audio board 69 which switches and mixes the sound which is connected to power amplifiers 71 for each of the four speakers 22 utilized which are shown in FIG. 1. In addition a talkover microphone 73 is provided in the master console 50 connected to the audio circuits 69 so that the tester can communicate with the subject or patient. These electronic circuits are of substantially conventional design and any suitable circuit may be employed which permits the objectives of the invention to be achieved.

Using pre-recorded noise and speech tapes, the speaker 22 level controls 81–88 can be varied to simulate a variety of three dimensional sound effects such as noise entering an open window in a car, shouts coming from ahead of, behind of or either side of the patient, radio music as the primary sound source or as background noise, telephone conversations or to simulate any other imaginable sound environment in which the patient may find himself or herself.

Interconnected to the operator's console 50 by an eight-conductor cable 47 is the patient's console 45 with four functional circuit modules. The front panel circuits 76–79 operate the patient accessible controls which include two variously colored light panels 92, 93, such as blue and orange, and a response mechanism 95, 96 for each to determine which of the light panels 92, 93 the patient has selected. Also shown in FIGS. 3 and 5 are the response buttons 95, 96 and separate right and left volume controls 98, 99 which the patient may rotate to adjust the gain or volume level of the aid when a hearing aid is being provided. It is this volume control 98 or 99 that is overridden by an override circuit 101 in master console 50 in the event the patient selects too low or too high a control setting rather than the most useful midrange positions. A similar conventional microcomputer system 77 consisting of a microprocessor and ROM and RAM memories with a communication module 78 is used to interconnect the subject console 45 to the master console 50.

Also connected to and controlled by the computer 77 in a manner to be discussed below are the hearing aid amplifiers 79 which are connected to the microphones and receiver which are located in the earshell assembly, and which include the integrated circuit amplifier and the various resistive and capacitance components shown in FIG. 11 which are used to establish various levels of S.S.P.L., gain and slope and separate volume controls for both right and left test modules 200. Both right and left test circuits 79 and modules 200 are provided so that the patient can individually test either ear and towards the end of testing have either or both test modules 200 in place while a final and complete check of the selected components is accomplished. Component selection and switching, which is one of the more important aspects of the invention, is discussed in more detail below in connection with the schematic diagrams of the circuits in the subject console as shown in FIGS. 11a–11d.

Referring now to the remaining schematics and curves, the patient's selection of the electronic characteristics and components of the final and finished hearing aid can be discussed and understood.

Figure 6:
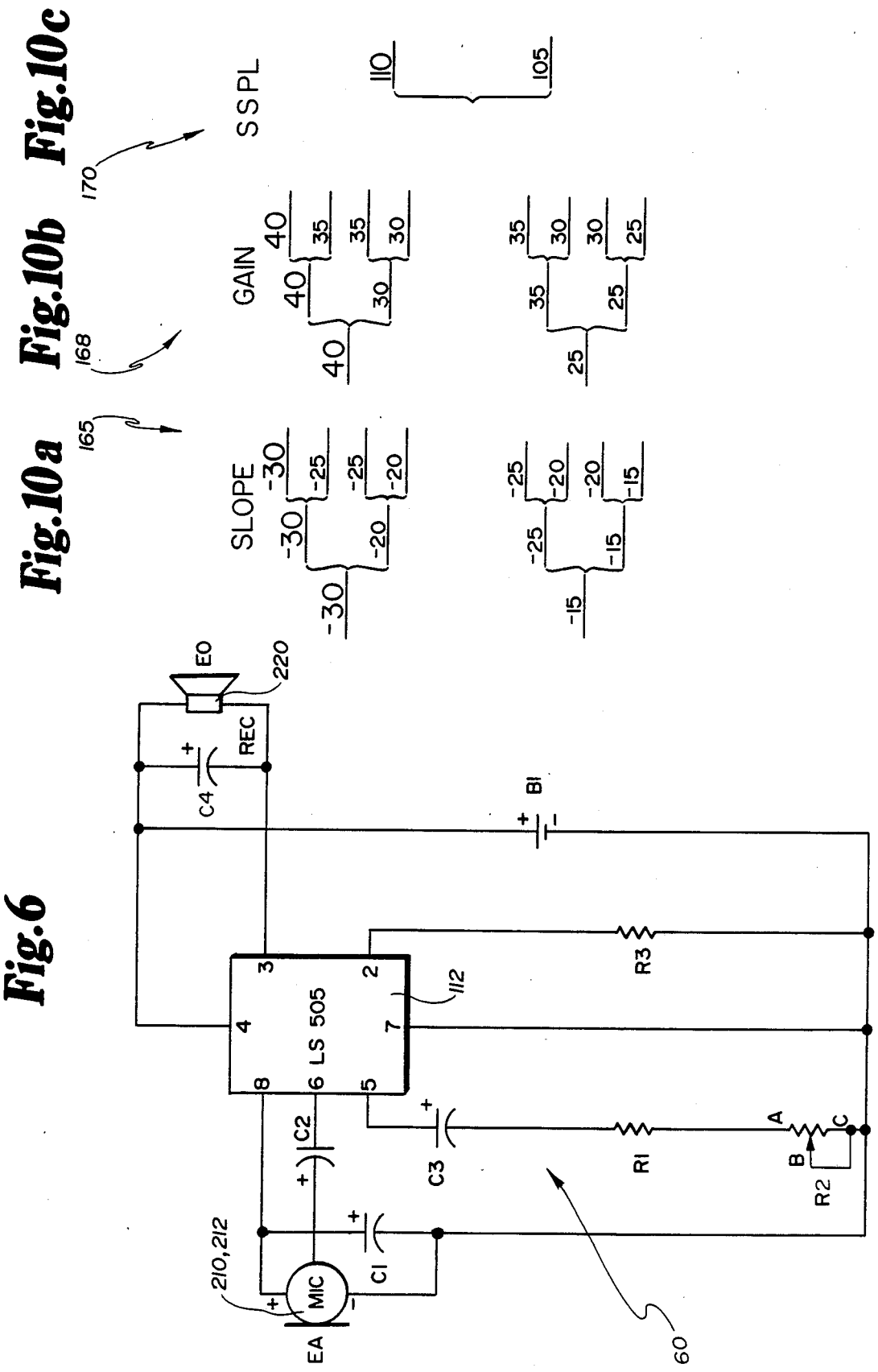
FIG. 6 is a schematic diagram of the electronic components which are used in the hearing aid which is produced as a result of testing by the patient controlled master aid.

FIG. 6 shows the electronic schematic of the final hearing aid. The components 60 of the hearing aid include a microphone 210 or 212 for a hearing aid or a pseudo-random noise generator 110 for a tinnitus masker, which is interconnected by resistors R1–R3 and capacitors C1–C4 through a hearing aid amplifier 112, manufacturers designation LS 505, manufactured by Linear Technology Incorporated. The amplifier 112 is also connected to a receiver 220 which provides the acoustic output of the hearing aid to the patient's eardrum.

Figure 7:
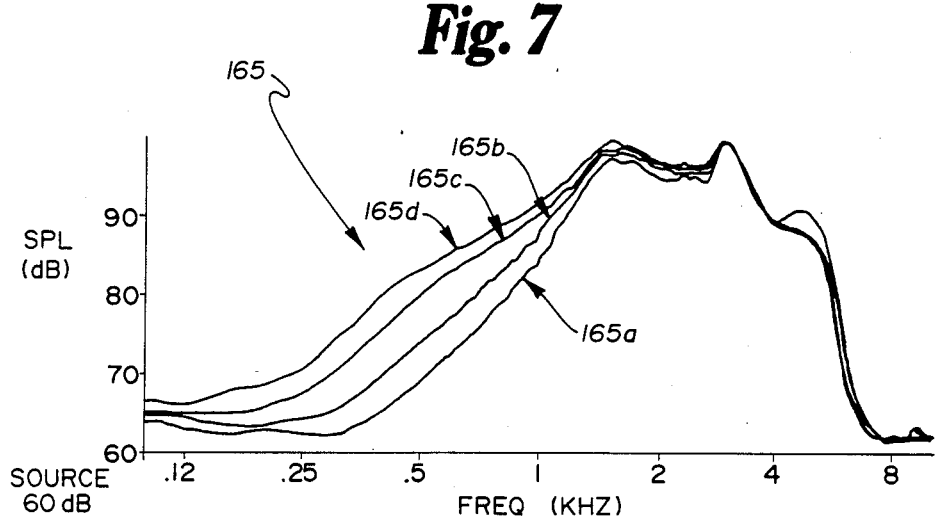
FIG. 7 is a family of matrix curves for an established S.S.P.L. and gain showing possible variations in slope which affect low frequency roll-off.

There are four selected components for the hearing aid or tinnitus masker that vary the sound response characteristics of the aid. To vary the frequency slope of response of the aid, as shown in FIG. 7, particularly the lower frequencies, the microphone 210 or 212 and the input coupling capacitor C2 may be varied. Selecting different combinations of those two components as shown in FIG. 10a, changes the low frequency roll-off. Two selectable microphones 210, 211 are provided, one with a fairly flat low frequency response and the other with a roll-off of the low frequency response. The selected microphone 210 or 211 in combination with the selected coupling capacitor C2 selects the aid's response to low frequency sounds. Similarly the selected capacitor C2 determines the low frequency response of a tinnitus masker when connected to a pseudo-random generator such as shown in FIG. 11b.

Figure 8:
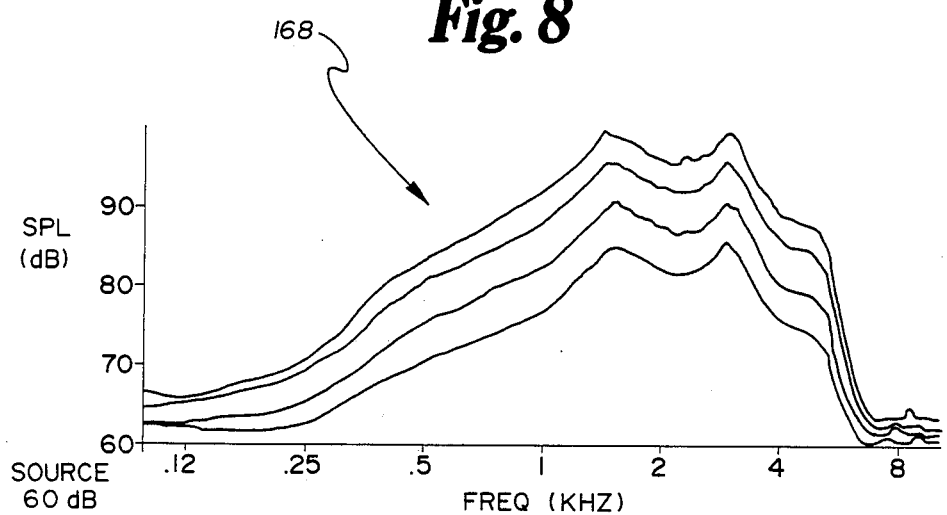
FIG. 8 is a similar family of matrix curves having a fixed saturation sound pressure level and fixed slope showing variations in gain.
Figure 9:
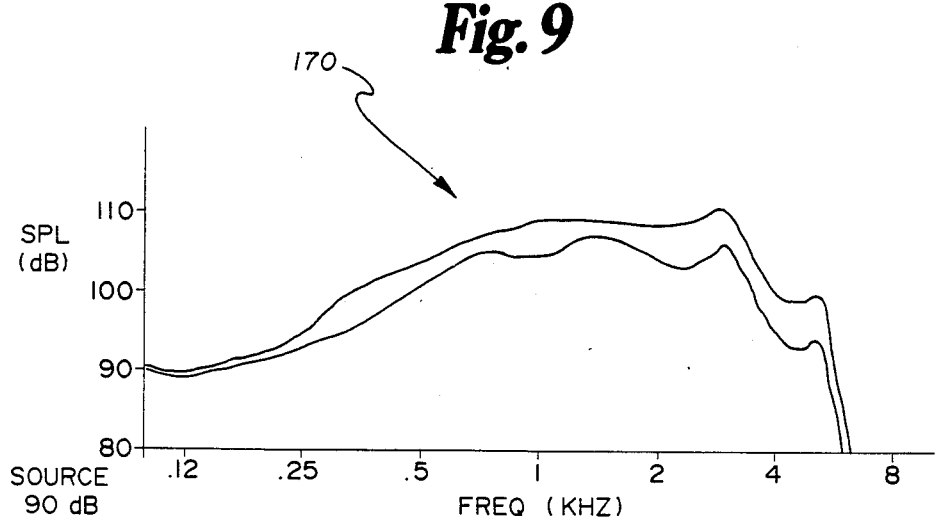
FIG. 9 is a family of matrix curve showing a fixed gain and a fixed slope showing changes in saturation sound pressure level.

Gain is selected by the value of R1 in series with the volume control R2. Maximum gain is achieved at a low resistance for R1 and the volume control R2 and as resistance R1 is increased the gain of the aid is decreased. Variations of gain of the amplifier are shown in FIG. 8 and a selection matrix is shown in FIG. 10b.

R3 selects the saturation sound pressure level of the aid. The saturation sound pressure level is the level of sound pressure that the aid cannot exceed, the level at which the amplifier saturates or reaches its maximum amplification. Two levels are shown in FIG. 11c. It will be understood, however, that additional levels can be easily achieved.

It will also be understood that there is interaction between the values selected for R1 and R3 which is accommodated by the test procedure. For example, for a maximum output level setting, such as one hundred ten dB selected by R3, the value used for a particular gain, such as thirty dB will yield a resistance value of two thousand ohms for R1. For the same gain at a one hundred five dB saturated sound pressure level, R1 would be 1600 ohms. These interrelated values are correlated in a look up table in software for the microcomputer 77 and switching is computer 77 controlled so that a patient selected gain of thirty dB will be presented through the hearing aid even if the related component for S.S.P.L. is varied during the test procedure.

Other parameters provided in the hearing aid circuit include the battery B-1 and capacitor C1, a bypass capacitor used to decouple the power supply battery B1 from the microphone supply. This capacitor C1 together with a resistor in the amplifier 112, provide low pass filter that decouples battery B1 voltage modulation from the microphone 210 or 211, effectively providing a slight increase in gain. The remaining capacitor, C4, is used to roll-off the high end of the output signal by effectively shorting out the very high end receiver frequencies.

At the start of a testing process or procedure a target stimulus sound to which the patient is to respond, such as continuous speech, is played through the speakers 22.

Background or environmental noise is combined with the target-stimulus with the mixing circuit in module 69.

Referring to FIGS. 1 and 2, the stimulus sound is played from the first tape deck 65 while an ambience noise level is created with the second tape deck 66, both of which are presented simultaneously through the speakers 22. Separate stimulus and ambience level controls 120-127 are provided for each of the four speakers 22. Visual level indication is provided by LED displays 140-147 associated with each of the eight speaker level controls 120-128. Hearing aid gain or volume controls 162, 163 and 98, 99 are also provided for a right test module 200 and a left test module 200 on both the operator's console 50 and patient's console 45. As indicated above, the operator may override the patient's volume control 98 or 99 with the volume control 162 or 163 on the operator's console 50 if the patient is not using the volume control 98 or 99 correctly or is having difficulty or discomfort. It is important for the professional to monitor the patient preferred volume control settings to insure that they lie within the most useful, mid-range, rather than at either extreme of the control.

Preferably two of the parameters are set by software or by the tester using the master console 50 at selected values and a third, the test parameter, is varied in a paired comparison tournament for selection by the patient. It is preferred for automated testing that S.S.P.L. 170 and gain 168 be set at their maximum settings and slope 165 be varied for the patient selection. Thereafter slope 165 is set at the patient preferred setting, S.S.P.L. 170 is left at the high range setting and gain 168 is varied for patient selection. And finally, slope 165 and gain 168 are set at the patient selected setting and S.S.P.L. 170 is varied for the patient.

Tinnitus testing is similar. The pseudo-random noise generator 110 is provided which connects through the amplifier 112 to the receiver 220.

Additional displays 55, operator controls or switches 57 and the talkover microphone 73 are provided on the operator's console so that the operator can selectively monitor and/or perform the testing process. LED displays 175, 176, 177, 178 are provided to monitor the patient comparison selection, the present values of frequency response the output levels of the speakers 22 relative to the patient's head position and the volume control setting chosen by the patient which can be varied by the operator with switches 162, 163. S.S.P.L., gain, slope or tinnitus selection switches 180 are provided as well as a full range of switch controls 183, 185 for the tape decks 65, 66 and the right and left test modules 200.

Overall sound quality is achieved by the tournament process of elimination and the sound quality selected by the patient will determine the characteristics of the sounds provided by the hearing aid. Some patients prefer a high frequency emphasis, treble-like sound quality where substantial low frequency energy is attenuated and which tends to enhance the ability to identify the information rich consonants of speech. Others will prefer a more natural full range response containing additional low frequency or bass energy. Prior to the commencement of the decision tree and selected components comparison process it is necessary to select a vent insert 134 shown in FIGS. 4e and 4f, which will affect the low frequency response of the hearing aid along with serving pressure equalization and feedback forestalling functions. Since hearing losses frequently occur in both ears, test modules 200 and circuits and controls are provided for both right and left aids and a final test run can be made with both modules in place.

Referring now to the schematic diagrams of FIG. 10 variations in the sound and selection of various parameters to change the sound response can be explained and understood. Referring to FIG. 10, a number of computer controlled input lines 300, 301 are provided for both the left module 200 and the right module 200. The circuitry is identical for both left and right test modules 200 and the circuitry for only one module will be explained, the left module, with the understanding that similar test provisions and circuits are provided and shown for the right module.

Switching of components is accomplished with analog switches A-1-A-4 which are activated by the computers 59, 73 upon appropriate command by the master console 30.

As shown in FIG. 4d, two microphones 210, 212 may be provided in the test module 200, one of the microphones having a flat, low frequency response and the other microphone having a sloped low frequency response. Either microphone 210, 212 can be selected with an analog switch A11 or A12. Alternatively, a pseudo-random noise generator 110 as shown in FIG. 12b, may be connected through analog switch A13 and utilized for tinnitus masking. All input sounds may also be disconnected and the signal source line grounded with an analog switch A14 for purposes of disabling the module 200.

Directly connected in series with the microphones 210, 212 and pseudo-random noise generator 110 are four coupling capacitors C17-C20, each of which can be connected either individually or in parallel by appropriate analog switches A2. Four slope levels are established, two for each selected microphone 210 or 212, to establish a patient preferred slope. Therefore, with gain 168 and S.S.P.L. 170 fixed at a selected setting, the patient can evaluate each of the four levels of slope 165 to determine the preferred low frequency response of the aid. Data is exchanged between the patient console 45 and operator's console 50 via a half-duplex serial communications channel 63, 47, 78 under microcomputer 59, 77 control.

The operator's console 50 selects values of S.S.P.L. 170, gain 168 and slope 165, which it communicates to the patient's console 45. The computer 77 in the patient's console 45, using a look-up table, selects the components required. The operator's console 50 also selects which light 92 or 93 on the patient's console 45 is to be illuminated. To avoid introducing a bias during testing, there is no fixed correspondence between a particular set of parameters and a light color.

Using the operator's console 50 the tester may initially implement a −30 dB slope 165a using MIC 2 and capacitor C20, concomitant with illuminating the orange light 92 on the patient console 45. Then a −15 dB slope 165d may be enabled using MIC 1 and capacitor C17 along with illumination of the blue light 93. The patient alternately listens to the frequency response at both slopes. Assuming the patient selects the −30 dB slope 165a as preferable and touches the response button 95 below the orange light 92, the sequence is repeated using first MIC 2 and capacitor C19 for a −20 dB slope 165b, then MIC 2 and capacitor C20 for a −30 dB slope 165a. If the patient again chooses the −30 dB slope 165a, the sequence is again repeated using MIC 1 and capacitor C18 and MIC 2 and capacitor C19 for a trial comparison between −25 dB slope 165b and −30 dB slope 165a with the winning slope 165 selection establishing the patient's ultimate preference (See FIG. 10a). It will be understood by those skilled in the art that additional slope 165 characteristics can be created with additional capacitors interconnected by additional analog switches.

The output of the coupling capacitor C17-C20 is connected to the microphone input of the LS 505 amplifier 112 which is shown in FIG. 11c. Connected to the gain input of the amplifier 112 are gain selection resistors R9-R14 which are selectably connectable either individually or in parallel, to the circuit by the microprocessor 77 through a series of analog switches A3.

Two of the gain selection resistors R9, R10 are switched through a pair of analog switches connected in parallel, A31, A32 and A33, A34 respectively. This serves to effectively cut the resistance of the analog switch A3 in half. In addition, the resistance values of the gain selection resistors R9-R14 are selected at a somewhat lower value (typically about 150 ohms less) than the design value of the corresponding resistor R1 in the hearing aid to compensate for the resistance of the analog switches A6 and the minimum resistance of the opto-isolated field-effect transistor (FET) U17 discussed below. A variable resistor 190 in series with the gain selection resistors R9-R14 is provided to further adjust the total resistance yielded by the variable resistor 190, gain selection resistor R9-R14, analog switch A6 and opto-isolated FET U17 so that is is equal to the design value for the hearing aid.

Assuming that the patient selected a −15 dB slope 165d with an initially preset S.S.P.L. of 110, the software or tester may again cycle the patient through the decision tree choices by presenting different gain pairs, for example 40 dB gain and 25 dB gain, and then 40 dB gain and 30 dB gain if the patient selects 40 dB gain (see FIGS. 8 and 11b).

The volume control R2 in the hearing aid is a variable resistor rather than a potentiometer or voltage divider. Maximum gain is reached with a volume control setting of zero ohms and increasing the volume control resistance R2 decreases the gain of the hearing aid.

In order for both the patient to control the volume control using touch controls 98 and 99 and to have the tester override the volume control, using slide controls 162, 163 the volume control resistance is simulated electronically. As shown in the schematic, this is achieved with an opto-isolated field-effect transistor U17 operating as a variable resistor. The field-effect transistor 193 is operated in a linear range of the ratio between the input current to the LED 194 versus the resistance of the field-effect transistor 193. Values of the resistance are achieved with a digital-to-analog converter (not shown) with precise analog steps, ranging from zero to −10 volts. This output voltage is connected to operational amplifier U16 which is a voltage-to-current converter circuit with the use of transistor Q1. The current range through transistor Q1, and thus through the LED 194, is zero to steps by the digital to analog circuit to create the variable resistance required.

The patient console 45 volume control 98 or 99 position is sensed by the microprocessor 77 through an analog-to-digital converter that monitors the volume control potentiometer 98 or 99 operated by the patient and generates a digital number proportional to the potentiometer position. That digital number is converted with the use of a lookup table in software to the discrete resistance values used in the variable resistor R2.

The battery B1 supply voltage is also simulated to conform to the nominal 1.35 volts and nominal output impedance of 8 ohms which are the design specifications for the battery B1 to be used in the aid.

Referring to FIG. 11a, a 2½ volt reference signal is divided by voltage divider resistors R3, R4 to a 1.35 volt level. The 1.35 volt level is buffered through operational amplifiers U3 configured to have a unity gain. The output is then connected through a resistance pair R5, R6 having a parallel resistance of 8 ohms, the output of which is connected to the hearing aid amplifier 112.

Finally, in the schematic two resistance levels R21, R22 are shown for selection of hearing aid component R3. The patient selection process is completed with selection of the preferred S.S.P.L. 170 through analog switches A4. It will be obvious to those skilled in the art that with the addition of more resistors more levels of S.S.P.L. 170 can be created for testing by the patient. As with the gain selection resistors R9-R14, the values of the S.S.P.L. selection resistors R21 and R22 are approximately 50 ohms lower than the design values for the corresponding resistor R3 in the hearing aid to compensate for the analog switch resistance. A variable resistor 195 is also provided for further adjustment of the overall resistance.

Testing and selection for tinnitus masking using the pseudo-random generator 110 shown in FIG. 11b and connected to the circuits through analog switch A13 is substantially the same.

As shown in FIG. 11b, a pseudo-random noise generator 110 is utilized to create a white noise which is connected through analog switch A13 and one of coupling capacitors C17-C20 to the amplifier 112. Using the same decision tree the patient can change the gain 168, slope 165 or S.S.P.L. 170 of the tinnitus masking noise to provide a patient selected tinnitus masker.

Using the above described testing apparatus and methods the patient with a hearing defect can personally select and choose which of a variety of components should be utilized in the resulting hearing aid. This enables a discrete number of preselected circuits 60 to be assembled in an automatable production facility to provide a variety of patient selectable amplification modules to the dispenser. When the final selection is made by the patient for either or both the right and left ear, the dispenser can simply snap the proper amplification module into the earshell assemblies 12 that the patient used during testing. The selected hearing aid is then inserted in the patient's ear.

If a patient has a specific or unusual sound environment in which the aid is to be used, the patient can be requested to take a tape recorder and record the sound while wearing a miniature microphone in each ear. The invention easily accommodates any such specific requirement by providing the separate tape deck for ambient or environmental noise, in which the patient's own environment can be established as a test condition.

If for some reason the assembled aid has any sound qualities or differences from that preferred and selected during testing, simple removal of the amplification module 60 and retesting is available and easily performed at one sitting.

Having described a specific embodiment of the invention and the manner of using it, it will be obvious to those skilled in the art that many other variations and adaptations of the invention can be made by those skilled in the art.

For example, the number of possible amplification selections is effectively unlimited. Additional resistors and/or capacitors and analog switches can easily expand the selectable values for S.S.P.L., slope or gain at a minimum of cost and effort. It will also be understood that both a hearing aid microphone and a tinnitus masker can be employed in the same aid. Similar changes can be made in other aspects of the invention. All such adaptations and modifications that are within the scope of the following claims are within the intendment of the invention.

Having described our invention we claim:

1. A system for providing a patient selectable hearing aid to a hearing impaired patient comprising:
   a plurality of prefabricated patient selectable earshell assemblies one of which will substantially conform to the diameter and geometry of the patient's ear;
   a hearing aid test module for insertion into the patient selectable earshell assembly configured to receive both ambient sound and test-signal sound and to pass amplified sound through to the patient's ear having certain sound response characteristics;
   paired comparison means operably connected to the hearing aid test module for discretely varying the sound response characteristics of the hearing aid test module such that the patient is presented with a pair of different sound response characteristics as a paired comparison;
   means for demarking the listening interval for each one of the pair of different sound response characteristics, the demarking means comprising selection means for permitting the patient to select one of the paired comparison.

2. The system of claim 1 further comprising: a hearing aid amplifier module for insertion into the patient selectable earshell assembly with the same sound response characteristics as the sound response characteristics of the hearing aid test module as chosen by the patient with the selection means.

3. The system of claim 2 wherein the paired comparison means comprises different combinations of electronic components for the hearing aid test module for selection and wherein the hearing aid amplifier module comprises a prefabricated hearing aid module with the same electrical specifications as the finally selected electronic components used in the paired comparison means.

4. The system of claim 1 wherein the demarking means comprise visual lights of different colors.

5. The system of claim 1 wherein the demarking means comprise at least one key pad which the patient depresses to listen to one of the different sound response characteristics.

6. A system for providing a hearing aid to a patient with a hearing impediment comprising:
   three or more speakers arrayed around the patient's head;
   a plurality of prefabricated earshell assemblies for patient selection, at least one of which has a diameter and geometry to conform to the patient's right ear and at least another of which has a diameter and geometry to conform to the patient's left ear;
   a selectively removable test module for insertion into the patient's selected earshell assembly to pass sound having certain amplified sound response characteristics through the test module to the patient's eardrum in the ear in which the test module is inserted;
   an operator's console comprising:
     at least two sound sources one of which produces ambience or environmental background sound and the other of which produces test-signal sounds;
     means for electronically mixing the sound from the sound sources and connecting the mixed sound to the speakers; and
   a patient console connected to the test module, the patient console comprising:
     selectable electronic components at least one of which varies the sound response characteristics of sound passing through the test module with the selection of components being made by the operator's console such that the patient is presented with a pair of different sound response characteristics as a paired comparison;
     at least two light panels each of which is alternatively activated for each of the paired comparison sound response characteristics;
     selection means for responding to one of the paired comparison sound response characteristics or light panels;
     separate volume controls to change the volume of sound passing through the left and right test modules;
   wherein both the patient console and the operator's console comprise means for transmitting the receiving data from and to the other console; and
   wherein the operator's console further comprises means for selecting the electronic components in the patient console such that the selections of electronic components are presented as a series of paired comparisons to the patient for a patient preferred selection of each of the paired comparisons.

7. The system of claim 6 wherein the patient console further comprises means for producing a pseudo-random noise for tinnitus masking and wherein the operator's console comprises means for selectively connecting the pseudo-random noise to the test module.

8. The system of claim 6 wherein the selectable electronic components are varied to vary the gain of the sound response characteristics of sound passing through the test module.

9. The system of claim 6 wherein the selectable electronic components are varied to vary the saturation sound pressure level of the sound response characteristics of sound passing through the test module.

10. The system of claim 6 wherein the selectable electronic components are varied to vary the slope of the frequency response of the sound response characteristics of sound passing through the test module.

11. A method of providing a patient selectable hearing aid during a single visit to a dispenser's office comprising:
   establishing a first sound signal simulating a background acoustical environment;
   establishing a second sound signal for testing purposes;
   mixing the first and second sound signals and presenting them to a hearing impaired patient;
   selecting one of a plurality of earshell assemblies, the selected earshell assembly conforming to the size and geometry of the patient's hearing impaired ear;
   selecting one of a plurality of venting conditions for the earshell assembly;

inserting a test module in the selected earshell assembly for modifying sound response characteristics of the established sound signals;

varying at least one of the sound response characteristics of the test module such that the patient is presented with a pair of different sound response characteristics as a paired comparison of two members;

choosing by patient selection which member of the paired comparison of sound response characteristics best aids the patient's hearing impediment; and providing to the patient during the same office visit that the testing takes place a prefabricated hearing aid having the same sound response characteristics as chosen by the patient to best aid the hearing impediment.

12. A test device for prescribing the electronic sound response characteristics of hearing aid for a patient with an impaired hearing condition comprising:

at least one test signal sound source for creating a sound to be listened to by the patient through electronic components to select preferred sound response characteristics of the sound as passed through the electronic components;

an operator test console for selectively determining the sound response characteristics to be presented to the patient through the electronic components;

means for presenting each of a set of pairs of different sound response characteristics as a paired comparison to the patient;

a test module for insertion into the patient's ear for receiving each of the paired comparisons so that the patient may choose which one of each paired comparison best assists the patient's hearing condition;

means for demarking the listening interval of each of the pair of different sound response characteristics; and means for permitting the patient to select one of each paired comparison.

13. A test device for prescribing the electronic sound resonse characteristics of a hearing aid for a patient with an impaired hearing condition comprising:

electronic circuit means for selectively creating varying sound response characteristics and presenting the sound response characteristics to the patient in paired comparisons;

means inserted into the patient's ear for receiving the paired comparisons of sound response characteristics so that the patient may choose which sound response characteristic best assist the patient's hearing condition; and means for enabling the patient to select which sound response characteristic best assists the patient's impaired hearing condition.

14. A test device for prescribing a hearing aid for a patient with an impaired hearing condition comprising:

an earshell assembly for insertion into the patient's ear;

a test module comprising a microphone and receiver contained within the earshell assembly;

variable amplifying means connected to the test module for varying amplified sound response characteristics of the sound and for presenting the amplified sound response characteristic in paired comparisons so that the patient can select which amplified sound response characteristic best assists the patient's impaired hearing condition; and means to indicate to the patient when each of the pair of sound response characteristics are being presented.

15. A patient controlled master hearing aid comprising:

a sound receiver for insertion into the patient's ear;

a patient console connected to the receiver comprising at least one volume control to vary the volume of sound passing through the receiver;

an operator's console connected to the patient console comprising:

at least one means for monitoring the volume of sound chosen by the patient on the patient console volume control; and means for varying the volume selected by the patient whereby the operator can override the selection of volume control chosen by the patient and independently control the volume of sound transmitted through the receiver.

16. A method for prescribing the electronic sound response characteristics of a hearing aid for a patient with an impaired hearing condition comprising:

creating a sound to be listened to by the patient through electronic components;

selectively determining the sound response characteristics to be presented to the patient through the electronic components and presenting each of a set of pairs of different sound response characteristics of the patient as paired comparisons;

presenting each paired comparison to the patient so that the patient may choose which one of each paired comparison best assists the patient's hearing condition; and demarking each sound response characteristic interval in each set of pairs of different sound characteristics so that the patient can select one of each paired comparison.

17. A method for prescribing the electronic sound response characteristics of a hearing aid for patient with an impaired hearing condition comprising:

inserting a receiver into the patient's ear so that the patient may choose which sound response characteristics of sound transmitted to the receiver best assists the patient's impaired hearing condition;

selectively presenting varying sound response characteristics to the patient by presenting each of a set of pairs of different sound response characteristics as paired comparisons the variations being caused by switching between different electrical components; and permitting the patient to select which sound response characteristic best assists the patients' impaired hearing condition;

providing a hearing aid with components the same as the electrical components which caused the sound response that the patient selected.

18. A method of prescribing a hearing aid for a patient with an impaired hearing condition comprising:

inserting an earshell assembly into the patient's ear;

inserting a test module comprising a microphone and receiver into the earshell assembly; and selectively varying the sound response characteristics of sound transmitted to the receiver in paired comparisons by establishing varying sets of pairs, each set generated with the same sound source with a different amplification characteristic;

presenting each of the sets of pairs of different sound response characteristics to the patient; and permitting the patient to manually select one of each sound response characteristic in each pair so that the patient can select which sound response characteristic best assists the patient's impaired hearing condition.

* * * * *